United States Patent [19]
Gaudry et al.

[11] Patent Number: 5,340,809
[45] Date of Patent: Aug. 23, 1994

[54] NEW 1-(ALKOXYBENZYL)PIPERAZINE AMIDE COMPOUNDS

[75] Inventors: Michel Gaudry, Fontenay le Fleury; Bruno Pfeiffer, Eaubonne; Pierre Renard, Versailles; Jean-François Renaud de la Faverie, Le Chesnay; Gérard Adam, Le Mesnil le Roi, all of France

[73] Assignee: ADIR et Compagnie, Courbevoie Cedex, France

[21] Appl. No.: 929,993

[22] Filed: Aug. 13, 1992

[30] Foreign Application Priority Data

Aug. 20, 1991 [FR] France ................ 91 10431

[51] Int. Cl.$^5$ ............... A61K 31/495; C07D 295/185; C07D 403/06
[52] U.S. Cl. .................... 514/252; 514/253; 514/255; 544/362; 544/365; 544/370; 544/372; 544/373; 544/391; 548/542
[58] Field of Search ............... 544/362, 365, 370, 372, 544/373, 391; 514/252, 253, 255

[56] References Cited

U.S. PATENT DOCUMENTS 4,997,836 3/1991 Sugihara et al. ............ 544/372
5,011,928 4/1991 Venero et al. ............ 544/391

FOREIGN PATENT DOCUMENTS 486386 5/1992 European Pat. Off. .

OTHER PUBLICATIONS

Rault et al, Chemical Abstracts, vol. 117, No. 111468 (1992) (Abstract for EP 486386, May 20, 1992).
Nippon Chemiphar Co, Chemical Abstracts, vol. 99, No. 195003 (1983).
Kimura et al, Chemical Abstracts, vol. 107, No. 198361 (1987).
The Merck Index, tenth edition, 1983, cover page and page 1209 concerning #8254 Scopolamine.
T. W. Robbins, "Neuropsychological evaluation of higher cognitive function in animals and man: can psychopharmacology contribute to neuropsychological theory?", Psychopharmacology, Recent advances and future prospects, (Edited by Susan D. Iversen), pp. 155–169 at p. 165 under heading Cholinergic Contributions to Cognition.

Primary Examiner—Emily Bernhardt

[57] ABSTRACT

A compound selected from those of formula (I):

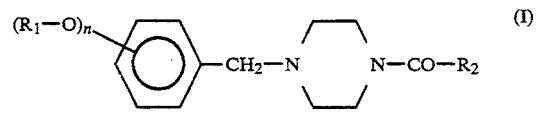

with $R_1$, $R_2$ and n as defined in the description, and medicinal products containing the same useful in treating or in preventing a disorder resulting from cellular damages following upon ischemia, hypoxia, or anoxia.

15 Claims, No Drawings

NEW 1-(ALKOXYBENZYL)PIPERAZINE AMIDE COMPOUNDS

The invention relates to new 1-(alkoxybenzyl)piperazine amide compounds, to process for preparing these and to pharmaceutical compositions containing them.

Many 1-(alkoxybenzyl)piperazine amide compounds are known in the literature.

Thus, some compounds of general formula (a):

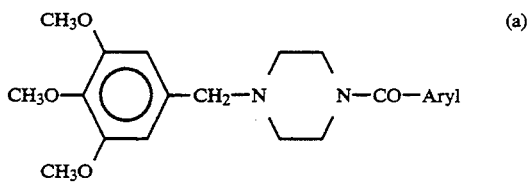

are described as Platelet Activating Factor or PAF antagonists (EP 318,235, EP 284,359).

Other compounds containing a 4-oxo-3-quinolyl group possess anti-inflammatory properties (JP 8,961,461), and compounds possessing a benzamide group are presented as carbonic anhydrase inhibitors (EP 171,636).

It is also noted that some 1-(alkoxybenzyl)piperazine cinnamides are described as antihypertensives (U.S. Pat. No. 4,368,199).

Structurally closer to the compounds of the invention, 1-(p-methoxybenzyl)piperazine pyroglutamide compounds are known in the literature, these being described as possessing nootropic activity (DE 3,701,494).

Compounds of formula (b):

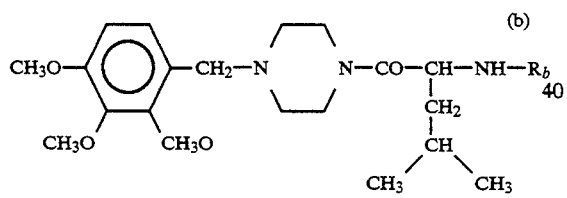

in which $R_b$ represents a protective group for the amine function of an amino acid, are also known, for which compounds no pharmacological activity has been mentioned and which are used as synthesis intermediates for compounds characterized by the presence of an oxirane ring and presented, in particular, as inhibitors of proteolytic enzymes (Biochemical Pharmacology 1985: vol. 34 (No. 21): 3875-3880 and Arzneim. Forsch. 1986: vol. 36 (No. 4): 671-675).

The Applicant has now discovered new alkoxybenzylpiperazine amide compounds which possess a markedly greater antiischemic and anti-anoxic action, at both cerebral and peripheral level, than that of the closest 1-(alkoxybenzyl)piperazines such as trimetazidine or 1-(2,3,4-trimethoxybenzyl)piperazine.

More specifically, the invention relates to the compounds of general formula (I):

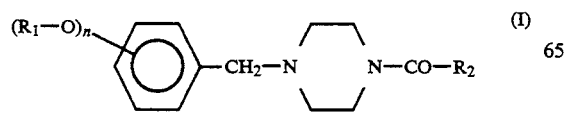

in which:

n, an integer, can take the values 1, 2 or 3, $R_1$ is a linear or branched alkyl containing from 1 to 4 carbon atoms, $R_2$ represents:

1) a group

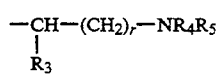

in which:

r, an integer, can take the values 0, 1 or 2, $R_3$ represents:

a) a hydrogen atom, b) a linear or branched alkyl having 1 to 6 carbon atoms, optionally substituted with one or two groups chosen from:

—COOH, —CO—$R_6$, —CO—O—$R_6$, with $R_6$ being a group chosen from: saturated, unsaturated or polyunsaturated, linear or branched alkyl having 1 to 12 carbon atoms, and —$(CH_2)_m$-aryl, optionally substituted, where m, an integer, can take the values 0, 1, 2 or 3, or with one group chosen from:

i) —OH, —O—$R_6$, —O—CO—$R_6$ or —O—CO—O—$R_6$, with $R_6$ as defined above, ii) —$NR_7R_8$, with $R_7$ and $R_8$, which may be identical or different, each representing, independently of one another, a hydrogen atom, a linear or branched alkyl having 1 to 6 carbon atoms, —CO—$R_6$ or —CO—O—$R_6$, with $R_6$ having the same meaning as above, and —$(CH_2)_m$-aryl, optionally substituted, where m, an integer, can take the values 0, 1, 2 or 3, iii) —CO—$NR_9R_{10}$, with $R_9$ and $R_{10}$, which may be identical or different, having the same definition as $R_6$ with $R_6$ as defined above, or also being able to represent a hydrogen atom, or $R_9$ and $R_{10}$, together with the nitrogen atom which bears them, form a 5- to 7-membered cyclic system which can optionally comprise a second hetero atom chosen from oxygen, nitrogen and sulfur, iv) —SH or —SeH, v) a group —S—$R_6$, —Se—$R_6$, —S—CO—O—$R_6$, —S—S—$R_6$ or —Se—Se—$R_6$, with $R_6$ as defined above, vi) a guanidino radical, unsubstituted or substituted with 1 to 2 groups chosen from nitro and —CO—O—$R_6$, with $R_6$ as defined above, vii) an indole or imidazole group, optionally substituted, c) a group —$(CH_2)_m$-phenyl, optionally substituted, where m, an integer, can take the values 0, 1, 2 or 3, on the understanding that $R_3$ cannot represent an isobutyl group, $R_4$ represents a hydrogen atom, a linear or branched alkyl having 1 to 6 carbon atoms, a group —$(CH_2)_p$-aryl, optionally substituted, where p, an integer, can take the values 0, 1, 2 or 3, or an amidino group, unsubstituted or substituted with a nitro group or a group —CO—O—$R_6$, with $R_6$ as defined above, or $R_4$, with $R_3$ and the atoms to which they are attached, forms a mono- or bicyclic system chosen from: pyrrolidine, piperidine, perhydroindole, indoline, 2-azabicyclo[2.2.2]octane and 2-aza-bicyclo[3.3.0]octane, it being possible for these cyclic systems to be optionally substituted with one or more groups chosen from:

hydroxyl, oxo, linear or branched alkyl having 1 to 6 carbon atoms, and linear or branched alkoxy having 1 to 6 carbon atoms, with the proviso that $R_3$ and $R_4$, together with the atoms to which they are attached, cannot form a pyrrolidine substituted with an oxo group the in the α-position with respect to the nitrogen, $R_5$ represents:

a hydrogen atom, a group $—(CH_2)_q$-aryl, optionally substituted, where q, an integer, can take the values 0, 1, 2 or 3, a saturated, unsaturated or polyunsaturated, linear or branched alkyl chain having 1 to 20 carbon atoms, optionally interrupted by one or more oxygen, sulfur or nitrogen atoms, and optionally substituted with one or more hydroxyl or amino radicals, linear or branched alkylamino radicals having 1 to 6 carbon atoms, or linear or branched alkoxy radicals having 1 to 6 carbon atoms, a group $—CO—R_{11}$ or $—CO—O—R_{11}$, where $R_{11}$ represents:

a saturated, unsaturated or polyunsaturated, linear or branched alkyl chain having 1 to 20 carbon atoms, optionally interrupted by one or more oxygen, sulfur or nitrogen atoms, and optionally substituted with one or more hydroxyl or amino radicals, linear or branched alkylamino radicals having 1 to 6 carbon atoms, linear or branched alkoxy radicals having 1 to 6 carbon atoms, guanidino radicals or guanidino radicals substituted with 1 to 2 groups chosen from nitro and $—CO—O—R_6$, with $R_6$ as defined above, a group $—(CH_2)_q$-aryl, optionally substituted, where q, an integer, can take the values 0, 1, 2 or 3, 2) a group:

$$-CH_2-CH-CH_2-N^{\oplus}(CH_3)_3$$
$$\underset{R_{12}}{\overset{O}{|}}$$

in which:

$R_{12}$ represents:

a hydrogen atom, a group $—CO—R_6$ or $—CO—O—R_6$, with $R_6$ having the same meaning as above, on the understanding that, except where otherwise specified: the term "aryl" means phenyl or naphthyl radical, the term "substituted" associated with the expressions "$—(CH_2)_m$-phenyl", $—(CH_2)_m$-aryl, "$—(CH_2)_p$-aryl", "$—(CH_2)_q$-aryl", "imidazole" and "indole" means that these radicals may be substituted on the ring with one or more groups chosen from: hydroxyl, halogen, nitro, trifluoromethyl, linear or branched alkyl having 1 to 6 carbon atoms, linear or branched alkoxy having 1 to 6 carbon atoms, $—(CH_2)_t$-phenyl, $—L—(CH_2)_t$-phenyl and $—O—CO—O—(CH_2)_t$-phenyl, where t, an integer, can take the values 0, 1, 2 or 3, and their isomers, diastereoisomers and epimers, isolated or in the form of a mixture, as well as, where appropriate, their addition salts with a pharmaceutically acceptable acid or base.

The subject of the present invention is also the process for preparing the compounds of formula (I), wherein, using coupling techniques which proceed via the formation of an activated ester (hydroxysuccinimide, hydroxybenzotriazole, in the presence of dicyclohexylcarbodiimide), a compound of formula (II):

$$HOOC—R'_2 \qquad (II)$$

in which $R'_2$ has the same meaning as $R_2$ in the general formula (I), with the proviso that, when $R'_2$ represents a group $$-CH-(CH_2)_r-NR_4R_5$$
$$\underset{R_3}{|}$$

as defined in the general formula (I) and when $R_4$ represents a hydrogen atom, then $R_5$ represents a group $—CO—R_{11}$ or $—CO—O—R_{11}$, with $R_{11}$ having the same meaning as in the general formula (I), is condensed with an (alkoxybenzyl)piperazine of formula (III):

$$(R_1—O)_n—\text{Ph}—CH_2—N\diagup\diagdown N—H \qquad (III)$$

in which $R_1$ and n are as defined in the formula (I), so as to obtain a compound of formula (I/a):

$$(R_1—O)_n—\text{Ph}—CH_2—N\diagup\diagdown N—CO—R'_2 \qquad (I/a)$$

in which $R_1$, $R'_2$ and n are as defined above, which compounds of formula (I/a) are, in the case where $R_5$ represents a group $—CO—O—R_{11}$, optionally subjected, if so desired, to the reactions of deprotection of the amine functions used in peptide synthesis (acid treatment or catalytic hydrogenation, depending on the nature of $R_{11}$), so as to gain access to the compounds of formula (I) for which $R_5$ represents a hydrogen, it then being possible for the compounds of formula (I) for which $R_5$ represents a hydrogen atom to be reacted, where appropriate, with a compound of formula (IV):

$$HOOC—R_{11} \qquad (IV)$$

in which $R_{11}$ is as defined above, so as to obtain a compound of formula (I/b):

$$(R_1—O)_n—\text{Ph}—CH_2—N\diagup\diagdown N—CO—CH—(CH_2)_r—\underset{R_3}{\overset{R_4}{N}}—CO—R_{11} \qquad (I/b)$$

in which $R_1$, $R_3$, $R_4$, $R_{11}$ and n are as defined above, a special case of the compounds of formula (I) in which $R_2$ represents a group of formula:

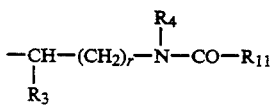

it being possible for the compounds of formula (I), if necessary, to be purified and separated, where appropriate, into their different optical isomers, and it also being possible for them to be salified, either with a pharmaceutically acceptable acid or, if it is possible and if so desired, with a pharmaceutically acceptable base.

The starting materials used in the process described above are
- either commercial,
- or readily accessible to a person skilled in the art according to processes described in the literature.

Compared to trimetazidine, the compounds of the present invention exhibit both in vivo and in vitro a very much greater cell-protective activity, in particular at cerebral level.

The tests carried out in vitro, on rat astrocytes in culture placed under hypoxic conditions, showed that the compounds of the present invention protected exceptionally well, and much better than trimetazidine, the cellular integrity of these astrocytes.

Other tests performed in vivo in gerbils showed that the compounds of the invention increased significantly, and very much better than trimetazidine, the survival of animals in which a cerebral ischemia is produced by ligation of the left carotid, and delayed considerably the onset of the first manifestations of suffocation in animals placed under conditions of normobaric hypoxia.

The remarkable properties of the compounds of the present invention make them invaluable, in particular at cerebral level, for the treatment and prevention of cerebral ischemia, cerebrovascular hypoxia, cerebrovascular anoxia and cerebral edema.

More generally, the protective power of the compounds of the present invention endows them with usefulness in the treatment of stroke, cranial trauma, encephalopathies, neurodegenerative diseases, and disorders of senescence.

The capacity of the compounds of the invention for protecting cells during hypoxia also enables them to be used in the treatment and prevention of peripheral type ischemia, in cardiology : myocardial ischemia and coronary ischemia and their various clinical expressions, namely angina pectoris, myocardial infarction, disorders of rhythm, vascular spasm and heart failure, as well as in ophthalmology and in otorhinolaryngology in the case of chorioretinal vascular pathologies, giddiness of vascular origin, Ménière's syndrome or tinnitus.

The invention also relates to the addition salts of the compounds of formula (I), obtained with a pharmaceutically acceptable, inorganic or organic base or acid.

Among pharmaceutically acceptable acids which may be used to form an addition salt with the compounds of the invention, there may be mentioned, by way of example and without implied limitation, hydrochloric, sulfuric, phosphoric, tartaric, malic, maleic, fumaric, oxalic, methanesulfonic, ethanesulfonic, camphoric and citric acids.

As pharmaceutically acceptable bases capable of salifying the compounds of formula (I), there may be mentioned, by way of example and without implied limitation, sodium, potassium, calcium or aluminum hydroxides, alkali metal or alkaline earth metal carbonates or, among organic bases, triethylamine, benzylamine, diethanolamine, tert-butylamine, dicyclohexylamine and arginine.

The invention also encompasses pharmaceutical compositions containing as active principle a compound of general formula (I), or one of its addition salts with a pharmaceutically acceptable, inorganic or organic base or acid, in combination with one or more non-toxic, inert excipients suitable for pharmaceutical use and/or a binding agent, a flavoring agent, a disintegrating agent, a sweetening agent and a lubricant, or alternatively a liquid vehicle suitable for intravenous administration, such as pyrogen-free sterile water.

Among the pharmaceutical compositions according to the invention, there may be mentioned, by way of example and without implied limitation, more especially those which are suitable for oral, parenteral, ocular, per- or transcutaneous, nasal, rectal, perlingual or respiratory administration, and in particular injections, aerosols, eye or nasal drops, tablets, sublingual tablets, capsules including hard gelatin capsules, troches, preparations to be placed under the tongue, suppositories, creams, ointments and gels.

The compositions thereby obtained are generally in the form of measured doses, and can contain, depending on the complaints being treated and the patient's age and sex, from 0.1 to 500 mg of active principle.

They can, depending on the case, be administered orally, rectally or parenterally, at a dose of 0.1 to 500 mg from one to several times a day.

The examples which follow illustrate the invention and in no way limit it.

EXAMPLE 1

1-(2,3,4-Trimethoxybenzyl)-4-(S-Benzyl-N-Benzyloxycarbonyl-L- Cysteinyl)Piperazine

Stage A :
N-[(S-benzyl-N-benzyloxycarbonyl-L-cysteinyl)oxy]succinimide 29.4 mmol of N-hydroxysuccinimide, dissolved in 30 cm$^3$ of methylene chloride, are added to 29.4 mmol of S-benzyl-N-benzyloxycarbonyl-L-cysteine dissolved in 20 cm$^3$ of methylene chloride. The mixture is cooled to 10° C. and 29.4 mmol of dicyclohexylcarbodiimide are then added.

The mixture is stirred for 4 hours at −10° C. and then for 1 hour at 20° C.

The dicyclohexylurea formed is removed by filtration and the solution of N- [(S-benyl-N-benzyloxy- carbonyl-L-cysteinyl)oxy]succinimide is used in the next step without further treatment.

Stage B :
1-(2,3,4-trimethoxybenzyl)-4-(S-benzyl-N-benzyloxycarbonyl-L-cysteinyl)piperazine The methylene chloride solution of N-[(S-benzyl-N-benzyloxycarbonyl-L-cysteinyl)oxy]succinimide obtained in the preceding stage is added to a solution, prepared beforehand and maintained at 4° C., of 29.4 mmol of 1-(2,3,4-trimethoxybenzyl)piperazine in 40 cm$^3$ of methylene chloride.

After 3 hours' stirring at 4° C. and 15 hours' stirring at 20° C., the medium is taken to dryness under reduced pressure and purified by chromatography on a silica column (eluent: chloroform/methanol (99:1), then chloroform/methanol (98:2)).

After the fractions collected are taken to dryness, 1-(2,3,4-trimethoxybenzyl)-4-(S-benzyl-N-benzyloxycarbonyl-L-cysteinyl)piperazine is obtained.

Optical rotation (c=1, absolute ethanol)
$[\alpha]_D^{20} = -21,7°$

Spectral characteristics:

Infrared ($CHCl_3$; 5 mg/cm$^3$; 0.1 mm) in cm$^{-1}$: 3000, 2920, 1705, 1635, 1485, 1460, 1250 and 1090.

$^1$H NMR ($CDCl_3$, internal reference: tetramethylsilane)

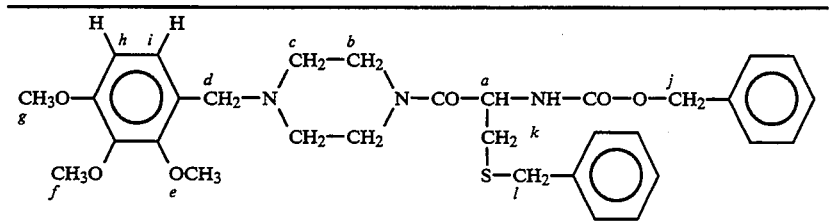

| 2.30–2.80 ppm; | triplet; | 4H; | c |
| 3.30–3.70 ppm; | triplet; | 4H; | b |
| 3.75 ppm; | singlet; | 2H; | d |
| 3.89 ppm; | 2 singlets; | 9H; | e, f, g |
| 4.78 ppm; | multiplet; | 1H; | a |
| 5.12 ppm; | singlet; | 2H; | j |
| 5.32 ppm; | singlet; | 2H; | l |
| 5.70 ppm; | doublet; | 1H; | —NH— |
| 6.65 and 6.95 ppm; | doublet; | 2H; | h, i (J=10Hz) |
| 7.22 ppm; | multiplet; | 5H; | phenyl |
| 7.33 ppm; | multiplet; | 5H; | phenyl |

Stage C:
1-(2,3,4-trimethoxybenzyl)-4-(S-benzyl-N-benzyloxycarbonyl-L-cysteinyl)piperazine hydrochloride The base obtained in stage B is suspended in 200 cm$^3$ of water. After acidification with hydrochloric acid until dissolution is complete (pH 2–3), the solution obtained is taken to dryness by lyophilization.

1-(2,3,4-Trimethoxybenzyl)-4-(S-benzyl-N-benzyloxycarbonyl-L-cysteinyl)piperazine hydrochloride is thereby obtained in the form of white crystals.

Optical rotation (c=1, absolute ethanol)
$[\alpha]_D^{20} = -11,8°$

EXAMPLE 2

1-(2,3,4-Trimethoxybenzyl)-4-(N-Benzyloxycarbonyl-L-Prolyl)Piperazine

Using the procedure described in Example 1, but replacing S-benzyl-N-benzyloxycarbonyl-L-cysteine in stage A by N-benzyloxycarbonyl-L-proline, 1-(2,3,4-trimethoxybenzyl)-4-(N-benzyloxycarbonyl-L-prolyl)-piperazine hydrochloride is obtained. Melting point (base) : 117° C.

Optical rotation (c : 1, absolute ethanol) (base):
$[\alpha]_D^{20} = -4,4°$

Optical rotation (c : 1, water) (hydrochloride):
$[\alpha]_D^{20} = -8,9°$

Spectral characteristics (base):

Infrared ($CHCl_3$; 5 mg/cm$^3$; 0.1 mm) in cm$^{-1}$: 3000, 2930, 1690, 1645, 1490, 1465, 1415, 1090.

$^1$H NMR ($CDCl_3$, internal reference: tetramethylsilane)

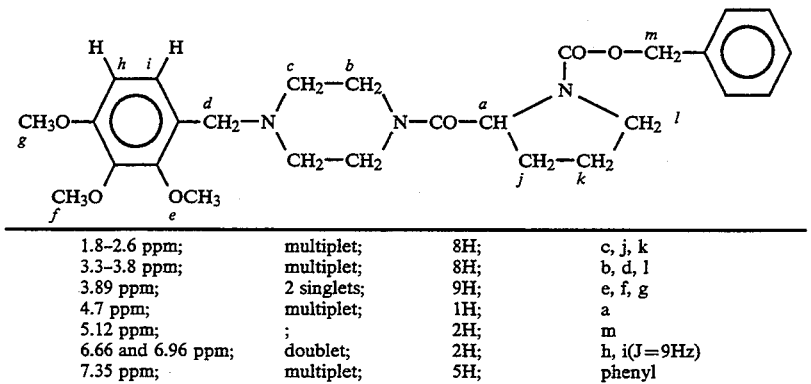

| 1.8–2.6 ppm; | multiplet; | 8H; | c, j, k |
| 3.3–3.8 ppm; | multiplet; | 8H; | b, d, l |
| 3.89 ppm; | 2 singlets; | 9H; | e, f, g |
| 4.7 ppm; | multiplet; | 1H; | a |
| 5.12 ppm; | ; | 2H; | m |
| 6.66 and 6.96 ppm; | doublet; | 2H; | h, i(J=9Hz) |
| 7.35 ppm; | multiplet; | 5H; | phenyl |

EXAMPLE 3

1-(2,3,4-Trimethoxybenzyl)-4-(L-Prolyl)Piperazine

A solution of 3 grams of 1-(2,3,4-trimethoxy-benzyl)-4-(N-benzyloxycarbonyl-L-prolyl)piperazine in 100 cm$^3$ of methanol is hydrogenated for 1 hour at a pressure of 1 bar of hydrogen in the presence of palladium on charcoal (10% Pd).

After removal of the catalyst by filtration and taking of the reaction medium to dryness, 1-(2,3,4- trimethoxybenzyl)-4-(L-prolyl)piperazine is obtained in the form of an oil in a quantitative yield of 100%.

This oil may be taken up in water to give, after acidification with 1N hydrochloric acid and isolation by lyophilization, 1-(2,3,4-trimethoxybenzyl)-4-(L-prolyl)-piperazine dihydrochloride.

EXAMPLE 4

1-(2,3,4-Trimethoxybenzyl)-4-(N-Benzyloxycarbonyl-S-Ethylthio-L-Cysteinyl)Piperazine Using the procedure described in Example 1, but replacing S-benzyl-N-benzyloxycarbonyl-L-cysteine by S-ethylthio-N-benzyloxycarbonyl-L-cysteine, 1-(2,3,4-trimethoxybenzyl)-4-(N-benzyloxycarbonyl-S-ethylthio-L-cysteinyl)piperazine hydrochloride is obtained.

EXAMPLE 5

1-(2,3,4-Trimethoxybenzyl)-4-(S-Ethylthio-L-Cysteinyl)Piperazine

Using the procedure described in Example 3, but replacing 1-(2,3,4-trimethoxybenzyl)-4-(N-benzyloxycarbonyl-L-prolyl)piperazine by 1-(2,3,4-trimethoxybenzyl)-4-(N-benzyloxycarbonyl-S-ethylthio-L-cysteinyl)- piperazine, 1-(2,3,4-trimethoxybenztyl)-4-(S-ethylthio-L-cysteinyl)piperazine dihydrochloride is obtained.

EXAMPLE 6

1-(2,3,4-Trimethoxybenzyl)-4-(N-Benzyloxycarbonyl-L-Alanyl)Piperazine

Using the procedure described in Example 1, but replacing S-benzyl-N-benzyloxycarbonyl-L-cysteine by N-benzyloxycarbonyl-L-alanine, 1-(2,3,4-trimethoxybenzyl)-4-(N-benzyloxycarbonyl-L-alanyl)piperazine hydrochloride is obtained.

Optical rotation (c=1, absolute ethanol) (base): $[\alpha]_D^{20} = -8,4°$

Optical rotation (c=1, water) (hydrochloride): $[\alpha]_D^{20} = 1°$

Spectral characteristics (base):

Infrared (CHCl$_3$; 5 mg/cm$^3$; 0.1 mm) in cm$^{-1}$: 3060, 2990, 1710, 1640, 1490, 1465, 1445, 1095.

$^1$H NMR (CDCl$_3$, internal reference: tetramethylsilane)

EXAMPLE 7

1-(2,3,4-Trimethoxybenzyl)-4-(L-Alanyl)Piperazine

Using the procedure described in Example 3, but replacing 1-(2,3,4-trimethoxybenzyl)-4-(N-benzyloxycarbonyl-L-prolyl)piperazine by 1-(2,3,4-trimethoxybenzyl)- 4-(N-benzyloxycarbonyl-L-alanyl)piperazine, 1-(2,3,4- trimethoxy benzyl)-4-(L-alanyl)piperazine dihydrochloride is obtained.

EXAMPLE 8

1-(2,3,4-Trimethoxybenzyl)-4-(N-Benzyloxycarbonyl-D-Alanyl)Piperazine

Using the procedure described in Example 1, but replacing S-benzyl-N-benzyloxycarbonyl-L-cysteine by N-benzyloxycarbonyl-D-alanine, 1-(2,3,4-trimethoxybenzyl)-4-(N-benzyloxycarbonyl-D-alanyl)piperazine hydrochloride is obtained.

Optical rotation (c=1, absolute ethanol): $[\alpha]_D^{20}$ base= +8,1°

EXAMPLE 9

1-(2,3,4-Trimethoxybenzyl)-4-(D-Alanyl)Piperazine

Using the prodedure described in Example 3, but replacing 1-(2,3,4-trimethoxybenzyl) 4-(N-benzyloxycarbonyl-L-prolyl)piperazine by 1-(2,3,4-trimethoxybenzyl)-4-(N-benzyloxycarbonyl-D-alanyl)piperazine, 1-(2,3,4-trimethoxybenzyl)-4-(D-alanyl)piperazine dihydrochloride is obtained.

EXAMPLE 10

1-(2,3,4-Trimethoxybenzyl)-4-(N-Benzyloxycarbonyl-L-Phenylalanyl)Piperazine

Using the procedure described in Example 1, but replacing S-benzyl-N-benzyloxycarbonyl-L-cysteine by N-benzyloxycarbonyl-L-phenylalanine, 1-(2,3,4-trimethoxybenzyl)-4-(N-benzyloxycarbonyl-L-phenylalanyl)piperazine hydrochloride is obtained.

Optical rotation (C=1, absolute ethanol): $[\alpha]_D^{20}$ (base)= +3,0° $[\alpha]_D^{20}$ (chlorhydrate)= +9,9°

Spectral characteristics (base):

Infrared (CHCl$_3$; 5 mg/cm$^3$; 0.1 mm) in cm$^{-1}$: 2980, 2900, 1710, 1635, 1490, 1460, 1090.

$^1$H NMR (CHCl$_3$, internal reference: tetramethylsilane)

| | | | |
|---|---|---|---|
| 1.09–1.18 ppm; | doublet; | 3H; | k |
| 2.46 ppm; | multiplet; | 4H; | c |
| 3.60 ppm; | multiplet; | 6H; | b, d |
| 3.91 ppm; | singlets; | 9H; | e, f, g |
| 4.63 ppm; | multiplet; | 1H; | a |
| 5.11 ppm; | singlet; | 2H; | j |
| 5.85 ppm; | doublet; | 1H; | —NH— |
| 6.65 and 6.95 ppm; | doublet; | 2H; | h, i(J=9Hz) |
| 7.32 ppm; | multiplet; | 5H; | phenyl |

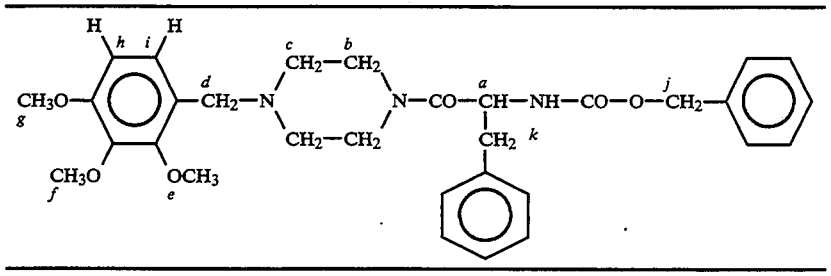

| | | | |
|---|---|---|---|
| 2.2–2.5 ppm; | multiplet; | 4H; | c |
| 3.39 ppm; | singlet; | 2H; | d |
| 3.40–3.60 ppm; | multiplet; | 4H; | b |
| 3.88 ppm; | 2 singlets; | 9H; | e, f, g |
| 4.89 ppm; | multiplet; | 1H; | a |
| 5.11 ppm; | singlet; | 2H; | j |
| 5.70 ppm; | doublet; | 1H; | —NH— |
| 6.64 and 6.90 ppm; | doublet; | 2H; | h, i,(J=8Hz) |
| 7.12–7.34 ppm; | multiplet; | 10H; | phenyl |

EXAMPLE 11

1-(2,3,4-Trimethoxybenzyl)-4-(L-Phenylalanyl)Piperazine

Using the procedure described in Example 3, but replacing 1-(2,3,4-trimethoxybenzyl)-4-(N-benzyloxycarbonyl-L-prolyl)piperazine by 1-(2,3,4-trimethoxybenzyl)-4-(N-benzyloxycarbonyl-L-phenylalanyl)piperazine, 1-(2,3,4-trimethoxybenzyl)-4-(L-phenylalanyl)-piperazine dihydrochloride is obtained.

EXAMPLE 12

1-(2,3,4-Trimethoxybenzyl)-4-[N-(Benzyloxycarbonyl)-Glycyl]Piperazine

Using the procedure described in Example 1, but replacing S-benzyl-N-benzyloxycarbonyl-L-cysteine in stage A by N-(benzyloxycarbonyl)glycine, 1-(2,3,4-trimethoxybenzyl)-4-[N-(benzyloxycarbonyl)glycyl]-piperazine hydrochloride is obtained.

EXAMPLE 13

1-(2,3,4-Trimethoxybenzyl)-4-Glycyl-Piperazine

Using the procedure described in Example 3, but replacing 1-(2,3,4-trimethoxybenzyl)-4-(N-benzyloxycarbonyl-L-prolyl)piperazine by 1-(2,3,4-trimethoxybenzyl)- 4-[N(benzyloxycarbonyl)glycyl]piperazine, 1-(2,3,4- trimethoxybenzyl)-4-glycylpiperazine dihydrochloride is obtained.

EXAMPLES 14 TO 46

Using the procedure described in Example 1, but replacing S-benzyl-N-benzyloxycarbonyl-L-cysteine in stage A by:

N-benzyloxycarbonyl-L-valine,
EXAMPLE 14 : 1-(2,3,4-TRIMETHOXYBENZYL)-4 -(N-BENZYLOXYCARBONYL-L-VALYL)PIPERAZINE is obtained.

N-benzyloxycarbonyl-4-aminobutyric acid,
EXAMPLE 15 : 1-(2,3,4-TRIMETHOXYBENZYL)-4-(N-BENZYLOXYCARBONYL-4-AMINOBUTYRYL)PIPERAZINE is obtained.

N-benzyloxycarbonyl-y-L-glutamic acid α-tert-butyl ester,
EXAMPLE 16 : 1-(,2,3,4-TRIMETHOXYBENZYL)-4-(N-BENZYLOXYCARBONYL-α-L-GLUTAMYL)PIPERAZINE TERT-BUTYL ESTER is obtained.

$N_\alpha, N_\delta, N_\omega$-tribenzyloxycarbonyl-L-arginine,
EXAMPLE 17: 1-(2,3,4-TRIMETHOXYBENZYL)-4-($N_\alpha, N_\delta, N_\omega$-TRIBENZYLOXYCARBONYL-L-ARGINYL)PIPERAZINE is obtained.

N-benzyloxycarbonyl-O-tert-butyl-L-tyrosine,
EXAMPLE 18 : 1-(2,3,4-TRIMETHOXYBENZYL)-4-(N-BENZYLOXYCARBONYL-O-TERT-BUTYL--L-TYROSYL)PIPERAZINE is obtained.

N-benzyloxycarbonyl-O-tert-butyl-L-threonine,
EXAMPLE 19 : 1-(2,3,4-TRIMETHOXYBENZYL)-4-(N-BENZYLOXYCARBONYL-O-TERT-BUTYL-L-THREONYL)PIPERAZINE is obtained.

N-benzyloxycarbonyl-O-tert-butyl-L-serine,
EXAMPLE 20 : 1-(2,3,4-TRIMETHOXYBENZYL)-4-(N-BENZYLOXYCARBONYL-O-TERT-BUTYL-L-SERYL)PIPERAZINE is obtained.

$N_\alpha$-benzyloxycarbonyl-$N_\epsilon$-tert-butyloxycarbonyl-L-lysine,
EXAMPLE 21 : 1-(2,3,4-TRIMETHOXYBENZYL)-4-($N_\alpha$-BENZYLOXYCARBONYL-$N_\epsilon$-TERT-BUTYLOXYCARBONYL-L-LYSYL)PIPERAZINE is obtained.

N-benzyloxycarbonyl-O-benzyl-D-tyrosine,
EXAMPLE 22: 1-(2,3,4-TRIMETHOXYBENZYL)-4-(N-BENZYLOXYCARBONYL-O-BENZYL-D-TYROSYL)PIPERAZINE is obtained.

$N_\alpha$-benzyloxycarbonyl-L-histidine,
EXAMPLE 23: 1-(2,3,4-TRIMETHOXYBENZYL)-4-BENZYLOXYCARBONYL-L-HISTIDYL)-PIPERAZINE is obtained.

N-benzyloxycarbonyl-α-L-aspartic acid β-tert- butyl ester,
EXAMPLE 24 : 1-(2,3,4-TRIMETHOXYBENZYL)-4-(N-BENZYLOXYCARBONYL-α-L-ASPARTYL)PIPERAZINE TERT-BUTYL ESTER is obtained.

$N_\alpha$-benzyloxycarbonyl-L-asparagine,
EXAMPLE 25: 1-(2,3,4-TRIMETHOXYBENZYL)-4-($N_\alpha$-BENZYLOXY CARBONYL -L-ASPARAGINYL)PIPERAZINE is obtained.

2-[1',3'-di(tert-butyloxycarbonyl)guanidino]- acetic acid,
EXAMPLE 26 : 1-(2,3,4-TRIMETHOXYBENZYL)-4-{2-[1',3'-DI(TERT-BUTYLOXYCAR- BONYL)GUANIDINO] ACETYL}PIPERAZINE is obtained.

2-(3'-tert-butyloxycarbonyl-1'-methylguanidino)acetic acid,

EXAMPLE 27 : 1-(2,3,4-TRIMETHOXYBENZYL)-4-[2-(3'-TERT-BUTYLOXYCARBONYL-1'-METHYL-GUANIDINO) ACETYL]PIPERAZINE is obtained.

3-[1',3'-di(tert-butyloxycarbonyl)guanidino]-propionic acid,

EXAMPLE 28 : 1-(2,3,4-TRIMETHOXYBENZYL)-4-{3- [1',3'-DI(TERT-BUTYLOXYCARBONYL)GUANIDINO]PROPIONYL}PIPERAZINE is obtained.

4-[1',3'-di(tert-benzyloxycarbonyl)guanidino]butyric acid,

EXAMPLE 29 : 1-(2,3,4-TRIMETHOXYBENZYL)-4-{4- [1',3'-DI(TERT-BUTYLOXYCARBONYL)-GUANIDINO]BUTYRYL} PIPERAZINE is obtained.

2-benzyloxycarbonylamino-4,4-di(tert-butyl-oxycarbonyl)butyric acid,

EXAMPLE 30: 1-(2,3,4--TRIMETHOXYBENZYL)-4-[2-BENZYLOXYCARBONYLAMINO-4,4-DI(TERT-BUTYLOXY CARBONYL) BUTYRYL]PIPERAZINE is obtained.

2-benzyloxycarbonylamino-3,3-di(tert-butyloxycarbonyl)propionic acid,

EXAMPLE 31 : 1-(2,3,4-TRIMETHOXYBENZYL)-4-[2- BENZYLOXY CARBONYLAMINO-3,3-DI(TERT-BUTYLOXY CARBONYL) PROPIONYL]PIPERAZINE is obtained.

$N_\alpha$-benzyloxycarbonyl-L-glutamine,

EXAMPLE 32 : 1-(2,3,4-TRIMETHOXYBENZYL)-4-($N_\alpha$-BENZYLOXY CARBONYL-L--GLUTAMINYL)PIPERAZINE is obtained.

N-benzyloxycarbonyl-y-trans-hydroxy-L-proline,

EXAMPLE 33 : 1-(2,3,4-TRIMETHOXYBENZYL)-4-(N- BENZYLOXY CARBONYL-Y-TRANS-HYDROXY-L-PROLYL)PIPERAZINE is obtained.

N-benzyloxycarbonyl-L-isoleucine,

EXAMPLE 34 : 1-(2,3,4-TRIMETHOXYBENZYL)-4-(N- BENZYLOXY CARBONYL-L-ISOLEUCYL)PIPERAZINE is obtained.

$N_\alpha$-benzyloxycarbonyl-N-nitro-L-arginine,

EXAMPLE 35 : 1-(2,3,4-TRIMETHOXYBENZYL)-4-($N_\alpha$- BENZYLOXY CARBONYL-$N_\omega$-NITRO-L-ARGINYL)PIPERAZINE is obtained.

N-benzyloxycarbonyl-L-methionine,

EXAMPLE 36 : 1-(2,3,4-TRIMETHOXYBENZYL)-4-(N- BENZYLOXY CARBONYL-L-METHIONYL)PIPERAZINE is obtained.

$N_\alpha$a-benzyloxycarbonyl-L-tryptophan,

EXAMPLE 37: 1-(2,3,4-TRIMETHOXYBENZYL)-4-($N_\alpha$- BENZYLOXY CARBONYL-L--TRYPTOPHYL)PIPERAZINE is obtained.

(2S,3aS,7aS)-N-benzyloxycarbonylperhydro-2indolecarboxylic acid,

EXAMPLE 38 : 1-(2,3,4-TRIMETHOXYBENZYL)-4-[(2S,3aS,7aS)-N-BENZYLOXYCARBONYL-PERHYDRO-2-INDOLYL CARBONYL]PIPERAZINE is obtained.

N,O-di(benzyloxycarbonyl)-L-tyrosine,

EXAMPLE 39 : 1-(2,3,4-TRIMETHOXYBENZYL)-4-[N,O-DI(BENZYLOXYCARBONYL)-L-TYROSYL]PIPERAZINE is obtained.

N,S-di(benzyloxycarbonyl)-L-cysteine,

EXAMPLE 40 : 1-(2,3,4-TRIMETHOXYBENZYL)-4 -[N,S-DI(BENZYLOXYCARBONYL)-L-CYSTEINYL]PIPERAZINE is obtained.

N-tert-butyloxycarbonyl-S-benzyl-L-cysteine,

EXAMPLE 41 : 1-(2,3,4-TRIMETHOXYBENZYL)-4-(N-TERT-BUTYLOXYCARBONYL-S-BENZYL-L-CYSTEINYL) PIPERAZINE is obtained.

N-pivaloyl-S-benzyl-L-cysteine,

EXAMPLE 42 : 1-(2,3,4-TRIMETHOXYBENZYL)-4-(N-PIVALOYL-S-BENZYL-L-CYSTEINYL)PIPERAZINE is obtained.

N-acetyl-S-benzyl-L-cysteine,

EXAMPLE 43 : 1-(2,3,4-TRIMETHOXYBENZYL)-4-(N-ACETYL-S-BENZYL-L-CYSTEINYL)-PIPERAZINE is obtained.

N-palmitoyl-S-benzyl-L-cysteine,

EXAMPLE 44 : 1-(2,3,4-TRIMETHOXYBENZYL)-4-(N-PALMITOYL-S-BENZYL-L-CYSTEINYL)PIPERAZINE is obtained.

N-eicosanoyl-S--benzyl--L-cysteine,

EXAMPLE 45 : 1-(2,3,4-TRIMETHOXYBENZYL)-4-(N-EICOSANOYL-S-BENZYL-L-CYSTEINYL)PIPERAZINE is obtained.

acetyl-DL-carnitine,

EXAMPLE 46: 1-(2,3,4-TRIMETHOXYBENZYL)-4-{[3-(TRIMETHYLAMMONIUM)-2-(ACETOXY)-1-PROPYL]CARBONYL}PIPERAZINE is obtained.

EXAMPLE 47

1-(2,5-Dimethoxybenzyl)-4-(S-Benzyl-N-Benzyloxycarbonyl-L-Cysteinyl)Piperazine

Using the procedure described in Example 1, but replacing 1-(2,3,4-trimethoxybenzyl)piperazine in stage B by 1-(2,5dimethoxybenzyl)piperazine, 1-(2,5-dimethoxybenzyl)-4-(S-benzyl-N-benzyloxycarbonyl-L-cysteinyl)piperazine hydrochloride is obtained.

EXAMPLES 48 TO 50

Using the procedure described in Example 1, but replacing 1-(2,3,4-trimethoxybenzyl)piperazine in stage B by 1-(2,5dimethoxybenzyl)piperazine and replacing S-benzyl-N-benzyloxycarbonyl-L-cysteine in stage A by N-benzyloxycarbonyl-L-proline, EXAMPLE 48: 1-(2,5-DIMETHOXYBENZYL)-4-(N-BENZYLOXY CARBONYL-L--PROLYL)PIPERAZINE is obtained.

by S-ethylthio-N-benzyloxycarbonyl-L-cysteine,

EXAMPLE 49 : 1-(2,5-DIMETHOXYBENZYL)-4-(S-ETHYLTHIO-N-BENZYLOXYCARBONYL-L-CYSTEINYL)PIPERAZINE is obtained.

by N-benzyloxycarbonyl-L-alanine,

EXAMPLE 50 : 1-(2,5-DIMETHOXYBENZYL)-4-(N-BENZYLOXY CARBONYL-L-ALANYL)PIPERAZINE is obtained.

EXAMPLE 51

1-(3-METHOXYBENZYL)-4-(S-BENZYL-N-BENZYLOXY CARBONYL-L-CYSTEINYL)PIPERAZINE

Using the procedure described in Example 1, but replacing 1-(2,3,4-trimethoxybenzyl)piperazine in stage B by 1-(3methoxybenzyl)piperazine, 1-(3-methoxybenzyl)- 4-(S-benzyl-N-benzyloxycarbonyl-L-cysteinyl)-piperazine hydrochloride is obtained.

EXAMPLES 52 TO 64

Using the procedure described in Example 3, but replacing 1-(2,3,4-trimethoxybenzyl)-4-(N-benzyloxycarbonyl-L-prolyl)piperazine by:

1-(2,3,4-trimethoxybenzyl)-4-(N-benzyloxycarbonyl-L-valyl)piperazine,

EXAMPLE 52 : 1-(2,3,4-TRIMETHOXYBENZYL)-4-(L-VALYL) PIPERAZINE is obtained.

1-(2,3,4-trimethoxybenzyl)-4-(N-benzyloxycarbonyl-4-aminobutyryl)piperazine,

EXAMPLE 53 : 1-(2,3,4-TRIMETHOXYBENZYL)-4-(4-AMINO BUTYRYL)PIPERAZINE is obtained.

1-(2,3,4-trimethoxybenzyl)-4-(N-benzyloxycarbonyl-α-L-glutamyl)piperazine γ-tert-butyl ester, EXAMPLE 54: 1-(2,3,4-TRIMETHOXYBENZYL)-4-(α-L-GLUTAMYL)PIPERAZINE TERT-BUTYL ESTER is obtained.

1-(2,3,4-trimethoxybenzyl)-4-(N-benzyloxycarbonyl-O-tert-butyl-L-tyrosyl)piperazine, EXAMPLE 55 : 1-(2,3,4-TRIMETHOXYBENZYL)-4-(O-TERT- BUTYL-L-TYROSYL)PIPERAZINE is obtained.

1-(2,3,4-trimethoxybenzyl)-4-(N-benzyloxycarbonyl-O-tert-butyl-L-seryl)piperazine, EXAMPLE 56 : 1-(2,3,4-TRIMETHOXYBENZYL)-4-(O-TERT-BUTYL-L-SERYL)PIPERAZINE is obtained.

1-(2,3,4-trimethoxybenzyl)-4-($N_\alpha$-benzyloxycarbonyl-$N_\epsilon$-tert-butyloxycarbonyl-L-lysyl)piperazine, EXAMPLE 57 : 1-(2,3,4-TRIMETHOXYBENZYL)-4-($N_\epsilon$-TERT-BUTYLOXYCARBONYL-L-LYSYL)PIPERAZINE is obtained.

1-(2,3,4-trimethoxybenzyl)-4-($N_\alpha$-benzyloxycarbonyl-L-histidyl)piperazine, EXAMPLE 58 : 1-(2,3,4-TRIMETHOXYBENZYL)-4-(L-HISTIDYL)PIPERAZINE is obtained.

1-(2,3,4-trimethoxybenzyl)-4-(N-benzyloxycarbonyl-L-glutaminyl)piperazine,

EXAMPLE 59 : 1-(2,3,4-TRIMETHOXYBENZYL)-4-(L-GLUTAMINYL)PIPERAZINE is obtained.

1-(2,3,4-trimethoxybenzyl)-4-{[(2S,3aS,7aS)-N-benzyloxycarbonylperhydro-2-indolyl]carbonyl}piperazine, EXAMPLE 60: 1-(2,3,4-TRIMETHOXYBENZYL)-4- [(2S,3aS,7aS)-PERHYDRO-2-INDOLYLCARBONYL]PIPERAZINE is obtained.

1-(2,5-dimethoxybenzyl)-4-(S-benzyl-N-benzyloxycarbonyl-L-cysteinyl)piperazine,

EXAMPLE 61 : 1-(2,5-DIMETHOXYBENZYL)-4-(S-BENZYL-L-CYSTEINYL)PIPERAZINE is obtained.

1-(2,5-dimethoxybenzyl)-4-(N-benzyloxycarbonyl-L-alanyl)piperazine,

EXAMPLE 62 : 1-(2,5-DIMETHOXYBENZYL)-4-(L-ALANYL) PIPERAZINE is obtained.

1-(3-methoxybenzyl)-4-(S-benzyl-N-benzyloxycarbonyl-L-cysteinyl)piperazine,

EXAMPLE 63 : 1-(3-METHOXYBENZYL)-4-(S-BENZYL-L-CYSTEINYL)PIPERAZINE is obtained.

1-(2,3,4-trimethoxybenzyl)-4-($N_\alpha, N_\delta, N_\omega$-tribenzyloxy carbonyl-L-arginyl)piperazine, EXAMPLE 64: 1-(2,3,4-TRIMETHOXYBENZYL)-4-(L-ARGINYL)PIPERAZINE is obtained.

EXAMPLE 65 : 1-(2,3,4-TRIMETHOXYBENZYL)-4-(L-LYSYL)PIPERAZINE 20 cm³ of trifluoroacetic acid are added to a solution of 0.9 gram of 1-(2,3,4-trimethoxybenzyl)-4-($N_\epsilon$- tert-butyloxycarbonyl-L-lysyl)piperazine in 20 cm³ of methylene chloride.

The mixture is left stirring for 20 min at 20° C. After evaporation of the methylene chloride and removal of the trifluoroacetic acid, 1-(2,3,4-trimethoxybenzyl)-4-(L-lysyl)piperazine is obtained in the form of an oil.

This oil may be taken up in water to give, after acidification with 1N hydrochloric acid and isolation by lyophilization, 1-(2,3,4-trimethoxybenzyl)-4-(L-lysyl)piperazine hydrochloride.

EXAMPLES 66 TO 70

Using the procedure described in Example 65, but replacing 1-(2,3,4-trimethoxybenzyl)-4-($N_\epsilon$-tert-butyloxycarbonyl-L-lysyl)piperazine by:

1-(2,3,4-trimethoxybenzyl)-4-($N_\alpha$-benzyloxycarbonyl-$N_\epsilon$-tert-butyloxycarbonyl-L-lysyl)piperazine, EXAMPLE 66 : 1-(2,3,4-TRIMETHOXYBENZYL)-4-($N_\alpha$-BENZYLOXYCARBONYL-L-LYSYL)PIPERAZINE is obtained.

1-(2,3,4-trimethoxybenzyl)-4-{2-[1',3'-di(tertbutyloxycarbonyl)guanidino]acetyl}piperazine, EXAMPLE 67 : 1-(2,3,4-TRIMETHOXYBENZYL)-4-(2-GUANIDINOACETYL)PIPERAZINE is obtained.

1-(2,3,4-trimethoxybenzyl)-4-[2-(3'-tert-butyloxycarbonyl-1'-methylguanidino)acetyl]piperazine, EXAMPLE 68: 1-(2,3,4-TRIMETHOXYBENZYL)-4-[2-(1'-METHYLGUANIDINO)ACETYL]PIPERAZINE is obtained.

1-(2,3,4-trimethoxybenzyl)-4-{3-[1',3'-di(tertbutyloxycarbonyl)guanidino]propionyl}piperazine, EXAMPLE 69 : 1-(2,3,4-TRIMETHOXYBENZYL)-4-(3-GUANIDINOPROPIONYL)PIPERAZINE is obtained.

1-(2,3,4-trimethoxybenzyl)-4-{4-[1',3'-di(tertbutyloxycarbonyl)guanidino]butyryl}piperazine, EXAMPLE 70 : 1-(2,3,4-TRIMETHOXYBENZYL)-4-(4-GUANIDINOBUTYRYL)PIPERAZINE is obtained.

EXAMPLE 71

1-(2,3,4-Trimethoxybenzyl)-4-(2-Amino-4,4-Dicarboxybutyryl)Piperazine

Using the procedure described in Example 3, but replacing 1-(2,3,4-trimethoxybenzyl)-4-(N-benzyloxycarbonyl-L-propyl)piperazine by 1-(2,3,4-trimethoxybenzyl)-4-[2-benzyloxycarbonylamino-4,4-di(tert-butyloxycarbonyl)butyryl]piperazine and then carrying out a step of mild acid hydrolysis, 1-(2,3,4-trimethoxybenzyl)-4-(2- amino-4,4-dicarboxybutyryl)piperazine is obtained.

EXAMPLE 72

1-(2,3,4-Trimethoxybenzyl)-4-(2-Amino-3,3-Dicarboxypropionyl)Piperazine

Using the procedure described in Example 71, but employing 1-(2,3,4-trimethoxybenzyl)-4-[2-benzyloxycarbonylamino-3,3-di(tert-butyloxycarbonyl)propionyl]piperazine in place of 1-(2,3,4-trimethoxybenzyl)-4-[2- benzyloxycarbonylamino-4,4-di(tert-butyloxycarbonyl)- butyryl]piperazine, 1-(2,3,4-trimethoxybenzyl)-4-(2-amino-3,3-dicarboxypropionyl)piperazine is obtained.

EXAMPLE 73

1-(2,3,4-Trimethoxybenzyl)-4-{2-[{4-[1',3'-Di(Tert-Butyloxycarbonyl)Guanidino]Butyryl}Amino]Acetyl} Piperazine Using the procedure described in Example 1, but replacing S-benzyl-N-benzyloxycarbonyl-L-cysteine in stage A by 4-[1',3'-di(tert-butyloxycarbonyl)guanidino]butyric acid and 1-(2,3,4trimethoxybenzyl)piperazine in stage B by 1-(2,3,4-trimethoxybenzyl)-4-glycylpiperazine obtained in Example 13, 1-(2,3,4-trimethoxybenzyl)-4-{2-[{4-[1',3'-di(tert-butyloxycarbonyl)-guanidino]butyryl}amino]acetyl}piperazine is obtained.

PHARMACOLOGICAL STUDY OF THE COMPOUNDS OF THE PRESENT INVENTION

EXAMPLE A

Testing for Antihypoxic Activity in Vitro

Principle:

Astrocytes in culture constitute a model of choice to test for cytoprotective activity when a hypoxic situation is confronted.

In effect, the first cellular reaction to be seen when the brain is under any kind of attack is a swelling of the astrocytes, even when the neurons, the oligodendrocytes and the endothelial cells still have a normal morphological profile.

In addition, it was recently shown that the astrocyte had a major role in the brain, in particular in the production of amino acid neurotransmitters and in the preservation of the extracellular ion balance (Rothman, S.M. et al., Ann. Neurol. (1986); 19: 105–111).

The Applicant hence tested the effect of the compounds of the invention on the cellular protection of astrocytes in culture placed in a hypoxic situation:
  by measuring the oxygen consumption of these astrocytes, thereby enabling the respiratory activity to be monitored,
  by analyzing certain enzyme markers, which enable the metabolic and membrane integrity of these astrocytes to be measured.

Methodology:

Rat astrocytes in primary culture are prepared from cortex obtained from brains of new-born rats.

The hypoxic treatment consists in exposing the cells in a humid atmosphere to a gaseous mixture consisting of 95% $N_2$ and 5% $CO_2$ at 37° C. for 15 hours.

The test compounds are added to the culture medium 12 hours before hypoxia. A second addition is carried out at the end of the hypoxic period.

2 hours after the end of hypoxia, the cellular oxygen consumption is measured, together with the intra- cellular and extracellular lactate dehydrogenase (LDH) enzyme activity and the ratio of the different LDH isoenzymes (heart isoenzyme/muscle isoenzyme or H/M).

a) Oxygen comsumption: The oxygen consumption of the cells is determined in an isotonic saline medium by polarimetric measurement in a GILSON oxygraph equipped with a Clark oxygen electrode.

b) Intracellular LDH activity: This is determined by spectrophotometric measurement at 340 nm on a cell extract obtained after ultrasonic disintegration of the cells.

c) Extracellular LDH activity: This is determined by spectrophotometric measurement at 340 nm on the culture medium.

d) H/M ratio: The different intracellular isoenzyme forms of LDH are estimated by electrophoresis in 7% polyacrylamide gel and specific identification of the isoenzyme bands.

Results:

The compounds of the invention permit a much larger improvement in respiratory activity (oxygen consumption) after hypoxia of the cells than that obtained after treatment with trimetazidine.

In addition, analysis of the different enzyme markers shows that the compounds of the invention exhibit an exceptional protective effect on metabolic integrity (intracellular LDH activity and isoenzyme ratio:H/M) and on membrane integrity (extracellular LDH activity).

As an example, 1-(2,3,4-trimethoxybenzyl)-4-(S- benzyl-N-benzyloxycarbonyl-L-cysteinyl)piperazine hydrochloride produces a 34% improvement in respiratory activity relative to untreated cells.

1-(2,3,4-Trimethoxybenzyl)-4-(S-benzyl-N-benzyloxycarbonyl-L-cysteinyl)piperazine hydrochloride also increases the value of the H/M ratio by more than 20%, an increase in the value of the ratio between the sign of good metabolic functioning, whereas a 17% drop in the value of this ratio is observed in untreated cells.

EXAMPLE B

Testing for Anti-Ischemic Activity in Vivo

Principle:

Some gerbils (40 to 60% of cases), termed sensitive, exhibit an abnormality of the circle of Willis (Levine et al., Exp. Neurol. 1966 ; 16 : 255–262).

As a result of this abnormality, the occlusion of a carotid in the gerbil makes it possible to reproduce, in contrast to other animal species, the pathology of human cerebral ischemia.

The Applicant has now tested the influence of the compounds of the invention on the survival of gerbils which have undergone a cerebral ischemia by ligation of the left carotid.

Methodology:

"Sensitive" gerbils are anesthetized intraperitoneally with Ketalar ® at a dose of 60 mg/kg. 30 minutes before ligation of the left carotid, various concentrations of the test compounds, dissolved in 3% polyethylene glycol, are administered intraperitoneally.

The behavior of the animals is analyzed at various times, and the signs observed are translated into a score according to the modified MacGraw index (MacGraw, CP et al.; Stroke (1976); 7:485). The statistical study is carried out according to the Mann-Whitney U test.

Results:

The compounds of the invention exhibit very considerable anti-ischemic protective activity, much greater than that of trimetazidine.

As an example, the percentage survival of the animals after ligation of the left carotid exceeds 70% at time 96 h under the action of 1-(2,3,4-trimethoxybenzyl)- 4-(S-benzyl-N-benzyloxycarbonyl-L-cysteinyl)piperazine hydrochloride, whereas all the animals are dead in the control experiments.

EXAMPLE C

Testing for Antihypoxic Activity in Vivo

Principle: C The animals (mice) are placed in a low-oxygen atmosphere, which induces the onset of manifestations of suffocation (or "gasps").

Compounds possessing antihypoxic properties produce a delay in the onset of these manifestations of suffocation.

The Applicant has now tested the compounds of the invention in this test.

Methodology:

Male mice (Swiss CD1) weighing 25–30 g are housed for 1 week before any experiment under standard animal house conditions (20°–22° C., 55% humidity, 12/12 light/ darkness cycle, industrial feed and water ad libitum).

The mice are placed in a box (7×5×5 cm) in which a low-oxygen atmosphere is created by the passage of a stream of air (96% $N_2$, 4% $O_2$, 12 l/min).

The delay in onset of the first manifestations of suffocation (or "gasps") is measured.

The animals receive a dose of the test compounds intraperitoneally 30 min before the production of hypoxia.

Vincamine (methyl 14,15-dihydro-14-hydroxyeburnamenine-14carboxylate) is used as a reference drug.

Results:

The results are presented in Table 1 for the compounds of the invention which is 1-(2,3,4-trimethoxybenzyl)-4-(S-benzyl-N-benzyloxycarbonyl-L-cysteinyl)- piperazine hydrochloride.

| TREATMENT | DOSE (mg/kg) | TIME ELAPSING BEFORE ONSET OF THE FIRST MANIFESTATIONS OF SUFFOCATION OR "GASPS" (in seconds) |
|---|---|---|
| CONTROL | — | 30 ± 7 |
| VINCAMINE | 2,5 | 48 ± 8 (not significant) |
| VINCAMINE | 20 | 167 ± 12 (significant) |
| 1-(2,3,4-TRIMETHOXYBENZYL) 4-[S-BENZYL N-BENZYLOXYCARBONYL L-CYSTEINYL] PIPERAZINE HYDROCHLORIDE | 2,5 | 70 ± 13 (significant) |

The results show that 1-(2,3,4-trimethoxybenzyl)-4-(S-benzyl-N-benzyloxycarbonyl-L-cysteinyl)piperazine hydrochloride is active as an antihypoxic at a dose of from 2.5 mg/kg, whereas the reference compound at the same dose does not produce any significant difference.

We claim:

1. A compound selected from those of formula (I):

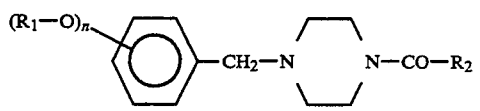

(I)

in which:

n, an integer, can take the values 1, 2 or 3, $R_1$ is linear or branched alkyl having 1 to 4 carbon atoms inclusive, $R_2$ represents:

1) a group

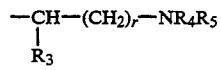

in which:

r, can take the values 0, 1 or 2, $R_3$ represents:

a) hydrogen, b) linear or branched alkyl having 1 to 6 carbon atoms, inclusive, optionally substituted with (I) one or two groups chosen from:

—COOH, —CO—$R_6$, —CO—O—$R_6$, with $R_6$ being a group chosen from: saturated or unsaturated linear or branched alkyl having 1 to 12 carbon atoms, inclusive, and —$(CH_2)_m$-aryl, optionally substituted, where m, can take the values 0, 1, 2 or 3, (II) or with one group chosen from:

i) —OH, —)—$R_6$, —O—CO—$R_6$ and —O—CO—O—$R_6$, with $R_6$ as defined above, ii) —$NR_7R_8$, with $R_7$ and $R_8$, which may be identical or different, each representing, independently of one another, hydrogen, linear or branched alkyl having 1 to 6 carbon atoms , inclusive, —CO—$R_6$ or —CO—O—$R_6$, with $R_6$ having the same meaning as above, and —$(CH_2)_m$-aryl, unsubstituted or optionally substituted, where m, can take the values 0, 1, 2 or 3, iii) —CO—$NR_9R_{10}$, with $R_9$ and $R_{10}$, which may be identical or different, having the same definition as $R_6$ as defined above, and also being able to represent hydrogen, iv) —SH or —SeH, v) a group —S—$R_6$, —Se—$R_6$, —S—CO—O—$R_6$, or S—S—$R_6$ with $R_6$ as defined above, vi) guanidino, unsubstituted or substituted with 1 to 2 groups chosen from nitro and —CO—O—$R_6$, with $R_6$ as defined above, vii) indol-3-yl or imidazol-4-yl, unsubstituted or optionally substituted, c) a group —$(CH_2)_m$-phenyl, unsubstituted or optionally substituted, where m, can take the values 0, 1, 2 or 3, with the proviso that $R_3$ cannot represent isobutyl, $R_4$ represents hydrogen, a linear or branched alkyl having 1 to 6 carbon atoms, inclusive, a group —$(CH_2)_p$-aryl, unsubstituted or optionally substituted, where p, can take the values 0, 1, 2 or 3, or amidino, unsubstituted or substituted with a nitro or a group —CO—O—$R_6$, with $R_6$ as defined above, or $R_4$, with $R_3$ and the atoms to which they are attached, forms a bicyclic heterocyclic system chosen from: perhydro-2-indolye, optionally substituted with one or more groups chosen from:
hydroxyl, oxo, linear or branched alkyl having 1 to 6 carbon atoms,inclusive, and linear or branched alkoxy having 1 to 6 carbon atoms, inclusive, $R_5$ represents:

hydrogen, a group —$(CH_2)_q$-aryl, optionally substituted, where q, can take the values 0, 1, 2 or 3, saturated or unsaturated linear or branched alkyl chain having 1 to 20 carbon atoms, inclusive, optionally interrupted by one or more oxygen, sulfur or nitrogen, and optionally substituted with one or more hydroxyl or amino, linear or branched alkylamino having 1 to 6 carbon atoms, inclusive, or linear or branched alkoxy having 1 to 6 carbon atoms, inclusive, a group —CO—$R_{11}$ or —CO—O—$R_{11}$, where $R_{11}$ represents:

saturated or unsaturated linear or branched alkyl having 1 to 20 carbon atoms, inclusive optionally interrupted by one or more oxygen or sulfur, and optionally substituted with one or more hydroxyl or amino, linear or branched alkylamino having 1 to 6 carbon atoms inclusive, linear or branched alkoxy having 1 to 6 carbon atoms inclusive, guanidino or guanidino unsubstituted or substituted with 1 to 2 groups chosen from nitro and —CO—O—$R_6$, with $R_6$ as defined above, or $R_{11}$ represents a group —$(CH_2)_q$-aryl, optionally substituted, where q, can take the values 0, 1, 2 or 3, $R_2$ represents 2) a group

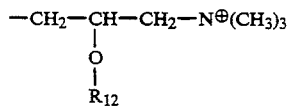

in which:

$R_{12}$ represents:

hydrogen, a group —CO—$R_6$ or —CO—O—$R_6$, with $R_6$ having the same meaning as above, with the proviso that, except where otherwise specified: the term "aryl" means phenyl or naphthyl, the term "substituted" associated with the expressions "—$(CH_2)_m$-phenyl", "—$(CH_2)_m$-aryl", "—$(CH_2)_p$-aryl", "—$(CH_2)_q$-aryl", "imidazol-4-yl" and "indol-3-yl" means that these radicals may be substituted on the ring with one or more groups chosen from: hydroxyl, halogen, nitro, trifluoromethyl, linear or branched alkyl having 1 to 6 carbon atoms inclusive, linear or branched alkoxy having 1 to 6 carbon atoms inclusive, —$(CH_2)_t$-phenyl, —O—$(CH_2)_t$-phenyl, and —O—CO—O—$(CH_2)_t$-phenyl, where t, can take the values 0, 1, 2 or 3, and its optical isomers, isolated or in the form of a mixture, as well as, where appropriate, its addition salts thereof with a Pharmaceutically-acceptable acid or base.

2. A compound selected from those as claimed in claim 1 for which n is equal to 3 and $R_1$ represents methyl, the three methoxy groups thus defined being borne at positions 2, 3 and 4 by the aromatic ring of the benzylpiperazine, corresponding to a compound of general formula (I α)

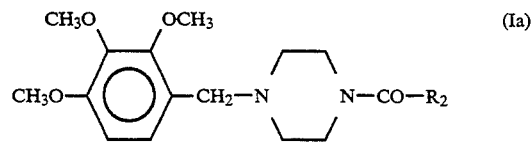

in which $R_2$ is as defined in claim 1, an optical isomer thereof, and an addition salt thereof with a pharmaceutically-acceptable acid or base.

3. A compound selected from those as claimed in claim 1 for which $R_2$ represents a group

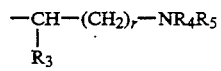

in which $R_3$ specifically represents a linear or branched alkyl having 1 to 6 carbon atoms, unsubstituted or substituted with —SH or —S—$R_6$, with $R_6$ as defined in claim 1, an optical isomer thereof, and an addition salt thereof with a pharmaceutically-acceptable acid or base.

4. A compound selected from those as claimed in claim 1 for which n is equal to 3, $R_1$ is methyl, the three methoxy groups thus defined being borne at positions 2, 3 and 4 by the aromatic ring of the benzylpiperazine, $R_2$ is a group

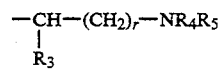

as defined in claim 1 for which $R_3$ represents linear or branched alkyl having 1 to 6 carbon atoms, inclusive, unsubstituted or substituted with —SH or a —S—$R_6$, with $R_6$ as defined in claim 1, an optical isomer thereof, and an addition salt thereof with a pharmaceutically-acceptable acid or base.

5. A compound selected from those as claimed in claim 1 for which $R_2$ represents a group

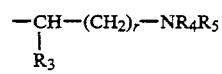

as defined in claim 1 in which $R_3$ and $R_4$, together with the atoms to which they are attached, form a bicyclic system chosen from: perhydro-2-indolyl optionally substituted with one or more groups chosen from:

hydroxyl, oxo, linear or branched alkyl having 1 to 6 carbon atoms, inclusive, and linear or branched alkoxy having 1 to 6 carbon atoms, inclusive, an optical isomer thereof, and an addition salt thereof with a pharmaceutically-acceptable acid or base.

6. A compound selected from those as claimed in claim 1 for which $R_3$ represents linear or branched alkyl having 1 to 6 carbon atoms, inclusive, optionally substituted with guanidino, unsubstituted or substituted with 1 to 2 groups chosen from nitro and —CO—O—$R_6$, with $R_6$ as defined in claim 1, an optical isomer thereof, and an addition salt thereof with a pharmaceutically-acceptable acid or base.

7. A compound as claimed in claim 1 selected from 1-(2,3,4trimethoxybenzyl)-4-(S-benzyl-N-benzyloxycarbonyl-L-cysteinyl)piperazine, an optical isomer thereof, and an addition salt thereof with a pharmaceutically-acceptable acid.

8. A compound as claimed in claim 1 selected from 1-(2,3,4-trimethoxybenzyl)-4-(N-benzyloxycarbonyl-L-alanyl)piperazine, an optical isomer thereof, and an addition salt thereof with a pharmaceutically-acceptable acid.

9. A compound as claimed in claim 1 selected from 1-(2,3,4-trimethoxybenzyl)-4-glycylpiperazine and an addition salt thereof with a pharmaceutically-acceptable acid.

10. A compound as claimed in claim 1 selected from 1-(2,5-dimethoxybenzyl)-4-(S-benzyl-L-cysteinyl)piperazine, an optical thereof isomer, and an addition salt thereof with a pharmaceutically-acceptable acid.

11. A compound as claimed in claim 1 selected from 1-(2,3,4-trimethoxybenzyl)-4-(L-arginyl)piperazine, an optical isomer thereof, and an addition salt thereof with a pharmaceutically-acceptable acid.

12. A compound as claimed in claim 1 selected from 1-(2,3,4-trimethoxybenzyl)-4-($N_\alpha$,$N_\delta$,$N_\omega$-tribenzyloxycarbonyl-L-arginyl)piperazine, an optical isomer thereof, and an addition salt thereof with a pharmaceutically-acceptable acid.

13. A compound as claimed in claim 1 selected from 1-(2,3,4-trimethoxybenzyl)-4-(2-amino-4,4-dicarboxybutyryl)piperazine, an optical isomer thereof, and an addition salt thereof with a pharmaceutically-acceptable acid or base.

14. A pharmaceutical composition useful in treating or in preventing a disorder resulting from cellular damages following upon ischemia, hypoxia, or anoxia containing as active principle an effective amount of a compound as claimed in claim 1, in combination with a pharmaceutically-acceptable excipient or vehicle.

15. A method of treating a mammal afflicted with a disorder resulting from cellular damages following upon ischemia, hypoxia, or anoxia comprising the step of administering to the said mammal an amount of a compound as claimed in claim 1 which is effective for alleviation of said disorder.

* * * * *

UNITED STATES PATENT AND TRADEMARK OFFICE
CERTIFICATE OF CORRECTION

PATENT NO. : 5,340,809
DATED : August 23, 1994
INVENTOR(S) : Michel Gaudry, Bruno Pfeiffer, Pierre Renard, Jean-Francois Renaud de la Faverie, Gèrard Adam It is certified that error appears in the above-indentified patent and that said Letters Patent is hereby corrected as shown below:

Column 3, line 66; "$-L-(CH_2)_t-$" should read -- $-O-(CH_2)_t-$ --
Column 10, line 67; the letters "lane)" need to be moved up to line 40 to read with the rest of the formula.
Column 12, line 29; move the "18" and the ":" next to "EXAMPLE"
Colunm 12, line 53; "-4-BENZYLOXYCARBONYL" should read
    -- -4-$N_\alpha$-BENZYLOXYCARBONYL --
Column 13, line 23; move the "30:" next to "EXAMPLE"
Column 19, line 4; delete the "C" after the word "Principle:"
Column 20, line 19; "-)-" should read -- -O- --
Column 21, line 1; "indolye" should read -- indolyl --

Column 22, line 17; insert (after the the formula)
    -- as defined in claim 1 --
Column 22, line 21; insert the word -- inclusive -- after the word "atoms"
Column 23, line 22; "thereof isomer," should read
    -- isomer thereof, -- (Resp. and Amdt. dated 6-28-93)

Signed and Sealed this

Sixth Day of December, 1994

Attest:

BRUCE LEHMAN

*Attesting Officer*     *Commissioner of Patents and Trademarks*